(12) United States Patent
Matthews et al.

(10) Patent No.: US 9,255,647 B2
(45) Date of Patent: Feb. 9, 2016

(54) DYNAMIC FLUID GAS BLEEDER MANIFOLD

(71) Applicant: Halliburton Energy Services, Inc., Houston, TX (US)

(72) Inventors: Kenneth Heidt Matthews, Houston, TX (US); Andrew David Vos, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 285 days.

(21) Appl. No.: 13/777,442

(22) Filed: Feb. 26, 2013

(65) Prior Publication Data

US 2014/0238495 A1  Aug. 28, 2014

(51) Int. Cl.
*F16L 41/00* (2006.01)
*F16K 27/00* (2006.01)
*G01N 33/28* (2006.01)

(52) U.S. Cl.
CPC ............ *F16K 27/00* (2013.01); *G01N 33/2823* (2013.01); *Y10T 137/0318* (2015.04); *Y10T 137/3084* (2015.04); *Y10T 137/87249* (2015.04)

(58) Field of Classification Search
CPC ......... B01F 5/0256; F16L 41/03; B60T 17/04
USPC ............................................. 137/597, 561 A
See application file for complete search history.

(56) References Cited

U.S. PATENT DOCUMENTS

| | | | |
|---|---|---|---|
| 1,960,746 A * | 5/1934 | Mailcry ........................ 123/327 |
| 3,095,929 A * | 7/1963 | McGuire et al. ............. 166/97.1 |
| 5,095,988 A * | 3/1992 | Bode ............................. 166/291 |
| 5,625,947 A * | 5/1997 | Crawford .................... 29/890.14 |
| 6,056,007 A * | 5/2000 | Gochenouer et al. ......... 137/351 |
| 6,176,262 B1 * | 1/2001 | Nimberger .................... 137/597 |
| 6,729,364 B2 * | 5/2004 | Few et al. ........................ 141/65 |
| 2001/0027817 A1 | 10/2001 | Giacomini |
| 2002/0100509 A1 | 8/2002 | Schlesch et al. |
| 2006/0038399 A1 * | 2/2006 | Tremoulet et al. ......... 285/124.5 |
| 2006/0130905 A1 | 6/2006 | Thelen |
| 2009/0107560 A1 | 4/2009 | Johnston |

FOREIGN PATENT DOCUMENTS

WO   2014133846 A1   9/2014

OTHER PUBLICATIONS

International Search Report and Written Opinion for PCT/US2014/017128 dated Jun. 16, 2014.

* cited by examiner

*Primary Examiner* — Craig Schneider
*Assistant Examiner* — Angelisa L Hicks
(74) *Attorney, Agent, or Firm* — McDermott Will & Emery LLP; Scott H. Brown

(57) ABSTRACT

Disclosed are high pressure test systems and methods. One dynamic fluid gas bleeder manifold includes gas outlet having opposing first and second ends and defining first opening at first end of gas outlet, wherein gas outlet extends between first and second ends along longitudinal axis of gas bleeder manifold, a first fluid inlet having opposing first and second ends defines second opening at first end of first fluid inlet, wherein first fluid inlet extends between first and second ends along first direction forming first acute angle with longitudinal axis, a second fluid inlet having opposing first and second ends defines third opening at first end of second fluid inlet, wherein second fluid inlet extends between first and second ends of second fluid inlet along second direction forming second acute angle with longitudinal axis, an internal fluid passage fluidly couples gas outlet to first and second fluid inlets.

20 Claims, 7 Drawing Sheets

DYNAMIC FLUID GAS BLEEDER MANIFOLD

BACKGROUND

The present disclosure relates to apparatuses and methods used with high pressure test systems. More particularly, the present disclosure relates to a dynamic fluid gas bleeder manifold.

High pressure dynamic fluid systems are used to simulate downhole conditions in a wellbore for an oil or natural gas well. High pressure dynamic fluid systems often contain gas pockets that corrupt the validity of instrumentation. Closed fluid systems, especially in high pressure applications, do not adequately address the need for intentional gas removal, and therefore, produce inaccurate exported data. The system must be bled at low pressure but remain resilient during high pressure operation.

FIG. 1 illustrates a conventional high pressure cross 10. As illustrated in FIGS. 2 and 3, in conventional high pressure crosses 10 with fixed devices, such as a pressure transducer 16 and a safety head 18, gas may be trapped in susceptible areas 17, such as the passageways leading to sensor heads 19, whether the cross 10 is used in a horizontal or vertical orientation, as shown in FIGS. 2 and 3, respectively. These gas pockets can create an inaccurate reading, and thereby taint any exported data.

SUMMARY OF THE DISCLOSURE

The present disclosure relates to apparatuses and methods used with high pressure test systems. More particularly, the present disclosure relates to a dynamic fluid gas bleeder manifold.

In some embodiments, the present disclosure provides a dynamic fluid gas bleeder manifold comprising a gas outlet having opposing first and second ends and defining a first opening on an outer surface of the manifold at the first end of the gas outlet, wherein the gas outlet extends between the first and second ends of the gas outlet along a longitudinal axis of the gas bleeder manifold. A first fluid inlet having opposing first and second ends defines a second opening on the outer surface at the first end of the first fluid inlet, wherein the first fluid inlet extends between the first and second ends of the first fluid inlet along a first direction forming a first acute angle with the longitudinal axis of the gas bleeder manifold, and forming a first obtuse angle with the gas outlet. A second fluid inlet having opposing first and second ends defines a third opening on the outer surface at the first end of the second fluid inlet, wherein the second fluid inlet extends between the first and second ends of the second fluid inlet along a second direction forming a second acute angle with the longitudinal axis of the gas bleeder manifold, and forming a second obtuse angle with the gas outlet. An internal fluid passage fluidly couples the gas outlet to the first and second fluid inlets such that a fluid can flow from the first fluid inlet to the second fluid inlet and gases transported by the fluid can exit the gas bleeder manifold through the gas outlet.

In other embodiments, the present disclosure provides a high pressure dynamic fluid test system comprising a dynamic fluid gas bleeder manifold comprising a gas outlet having opposing first and second ends and defining a first opening on an outer surface of the manifold at the first end of the gas outlet, wherein the gas outlet extends between the first and second ends of the gas outlet along a longitudinal axis of the gas bleeder manifold. A first fluid inlet having opposing first and second ends defines a second opening on the outer surface at the first end of the first fluid inlet, wherein the first fluid inlet extends between the first and second ends of the first fluid inlet along a first direction forming a first acute angle with the longitudinal axis of the gas bleeder manifold, and forming a first obtuse angle with the gas outlet. A second fluid inlet having opposing first and second ends defines a third opening on the outer surface at the first end of the second fluid inlet, wherein the second fluid inlet extends between the first and second ends of the second fluid inlet along a second direction forming a second acute angle with the longitudinal axis of the gas bleeder manifold, and forming a second obtuse angle with the gas outlet. An internal fluid passage fluidly couples the gas outlet to the first and second fluid inlets such that a fluid can flow from the first fluid inlet to the second fluid inlet and gases transported by the fluid can exit the gas bleeder manifold through the gas outlet. A pump is fluidly coupled to the gas bleeder manifold and configured to convey the fluid thereto. A sensor is fluidly coupled to the gas bleeder manifold and configured to measure a parameter of the fluid.

In still other embodiments, the present disclosure provides a method for high pressure testing a fluid, comprising providing a high pressure test system comprising a dynamic fluid gas bleeder manifold comprising a gas outlet having opposing first and second ends and defining a first opening on an outer surface of the manifold at the first end of the gas outlet, and the gas outlet extends between the first and second ends of the gas outlet along a longitudinal axis of the gas bleeder manifold. A first fluid inlet having opposing first and second ends defines a second opening on the outer surface at the first end of the first fluid inlet, wherein the first fluid inlet extends between the first and second ends of the first fluid inlet along a first direction forming a first acute angle with the longitudinal axis of the gas bleeder manifold, and forming a first obtuse angle with the gas outlet. A second fluid inlet having opposing first and second ends and defines a third opening on the outer surface at the first end of the second fluid inlet, wherein the second fluid inlet extends between the first and second ends of the second fluid inlet along a second direction forming a second acute angle with the longitudinal axis of the gas bleeder manifold, and forming a second obtuse angle with the gas outlet. An internal fluid passage fluidly couples the gas outlet to the first and second fluid inlets such that a fluid can flow from the first fluid inlet to the second fluid inlet and gases transported by the fluid can exit the gas bleeder manifold through the gas outlet. The test system further comprises a pump communicating with the gas bleeder manifold to pump the fluid, and a sensor for measuring a parameter of the fluid. A fluid is provided to the high pressure test system. The fluid is pumped to increase the pressure on the fluid and a parameter of the fluid is measured.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present disclosure relates to apparatuses and methods used with high pressure test systems. More particularly, the present disclosure relates to a dynamic fluid gas bleeder manifold.

A dynamic fluid gas bleeder manifold according to the present disclosure uses a specific geometry and orientation to assist in the transport and removal of gas from critical system zones as well as maintaining a closed system after it has been bled.

Figure 1:
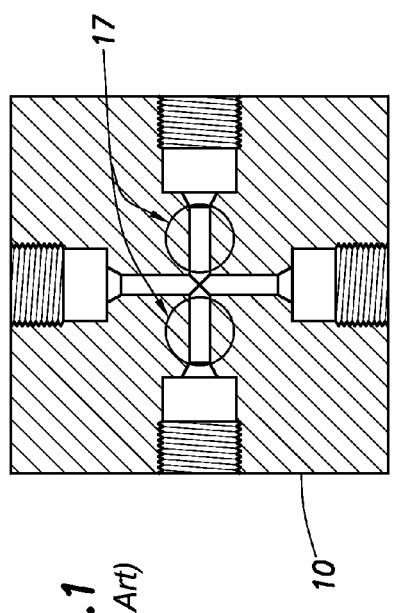
FIG. 1 is a cross-sectional view of a conventional high pressure cross.
Figure 2:
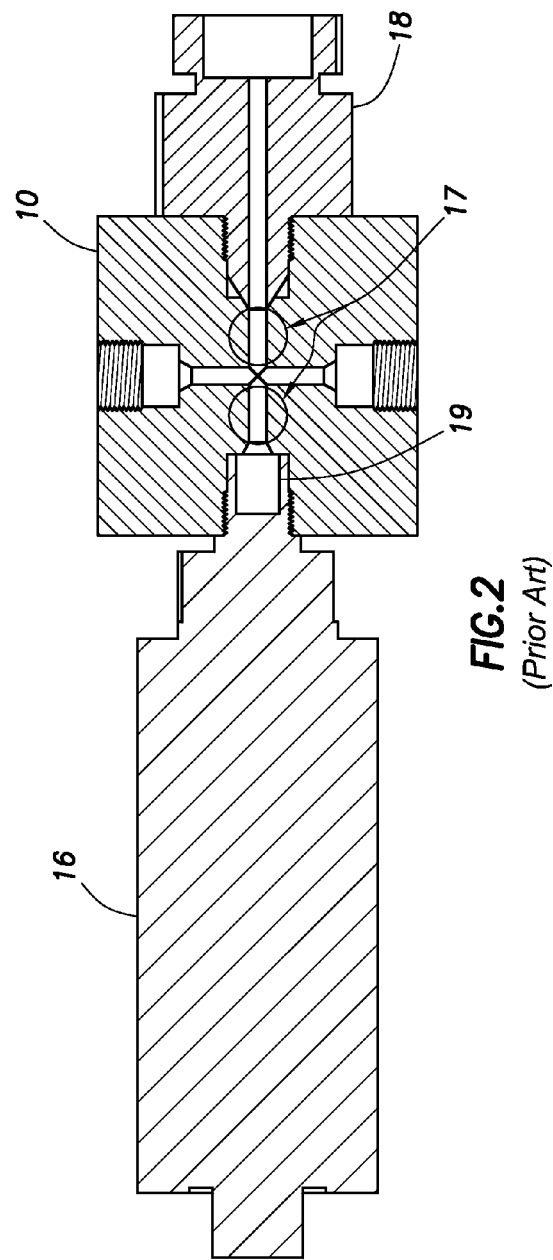
FIG. 2 is a cross-sectional view of a conventional high pressure cross with fixed devices in a horizontal orientation.
Figure 3:
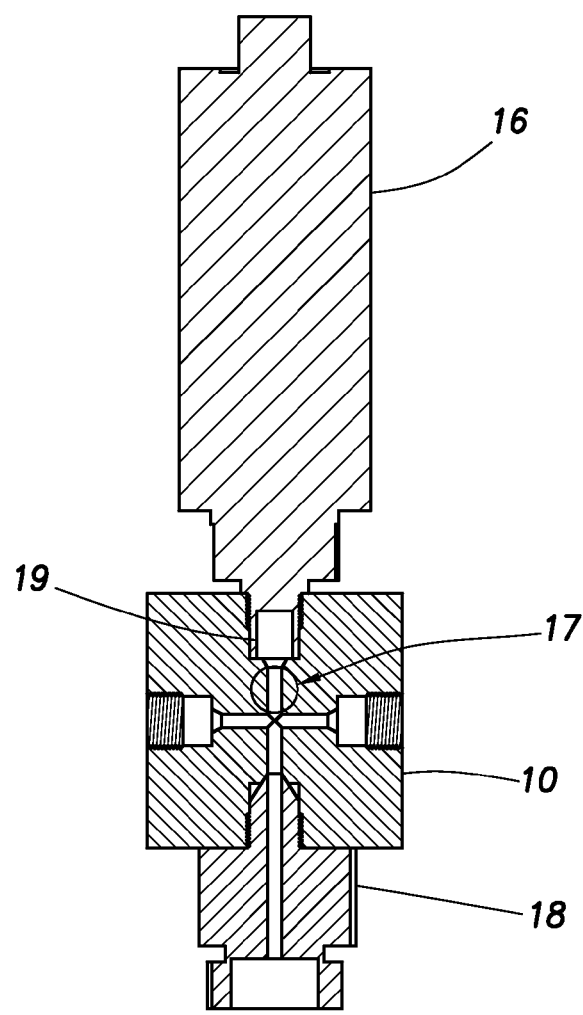
FIG. 3 is a cross-sectional view of a conventional high pressure cross with fixed devices in a vertical orientation.
Figure 4:
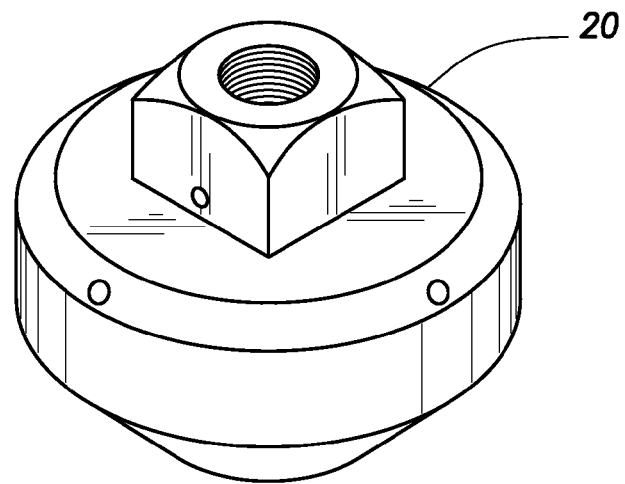
FIG. 4 is an isometric view of a dynamic fluid gas bleeder manifold according to an embodiment of the present disclosure.
Figure 5:
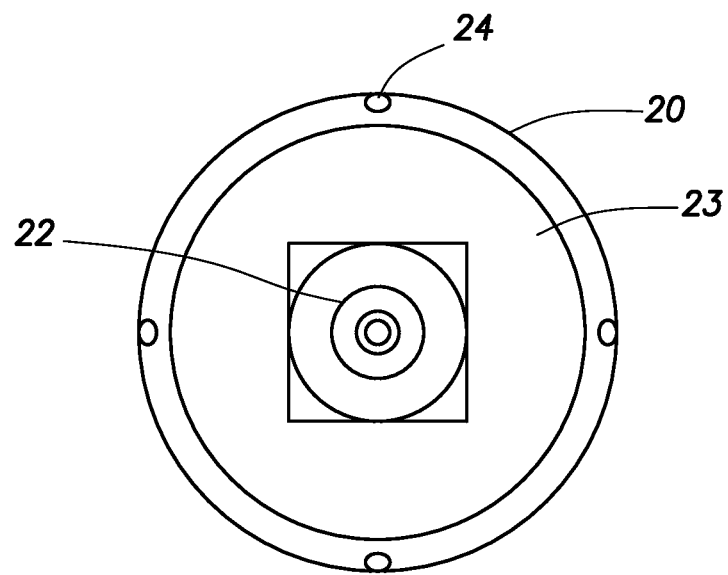
FIG. 5 is a plan view of a dynamic fluid gas bleeder manifold according to an embodiment of the present disclosure.

A dynamic fluid gas bleeder manifold 20 according to an embodiment of the present disclosure is illustrated in FIG. 4. In certain embodiments of the present disclosure the dynamic fluid gas bleeder manifold 20 is substantially circular-shaped as seen in plan view in FIG. 5. A gas outlet 22 is located on an upper portion 23 of the manifold 20. Fluid inlets 26 are located on lower portions 27 of the manifold 20, as illustrated in FIG. 6 (only one fluid inlet 26 shown).

Figure 6:
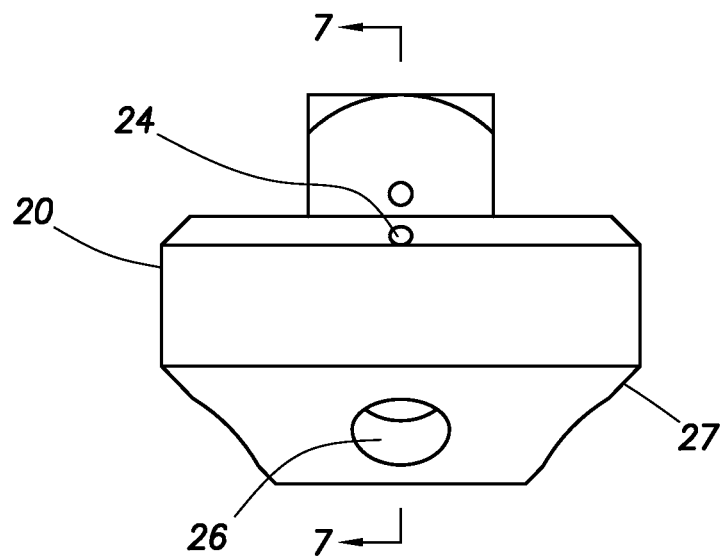
FIG. 6 is a side view of a dynamic fluid gas bleeder manifold according to an embodiment of the present disclosure.
Figure 7:
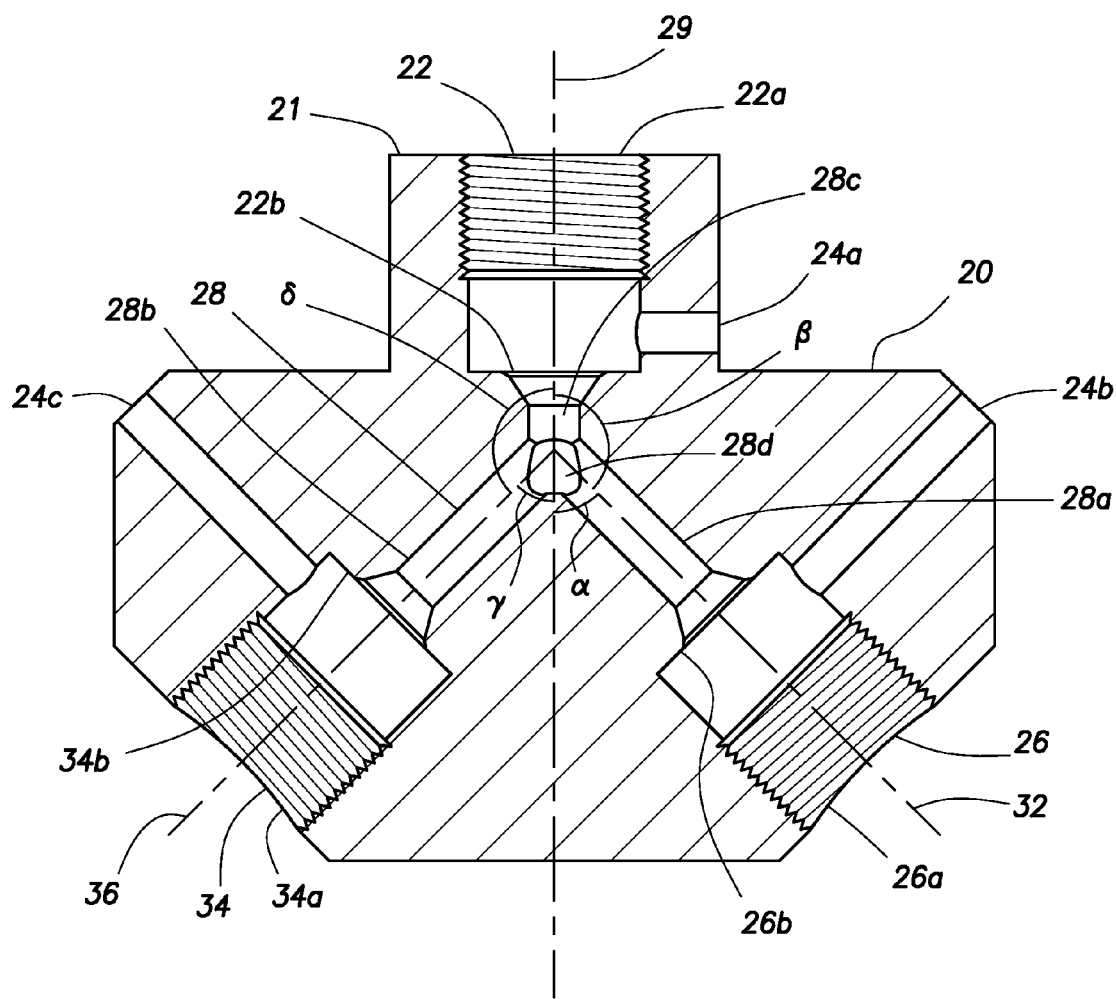
FIG. 7 is a cross-sectional view of a dynamic fluid gas bleeder manifold according to an embodiment of the present disclosure.

Adverting to FIG. 7, illustrating a cross-section of FIG. 6 taken along lines 7-7 in FIG. 6, the dynamic fluid gas bleeder manifold 20 according to an embodiment of the present disclosure is described in greater detail. The gas outlet 22 has opposing first and second ends 22a, 22b and defines a first opening on an outer surface of the manifold 21 at the first end 22a of the gas outlet 22, wherein the gas outlet 22 extends between the first and second ends 22a, 22b of the gas outlet 22 along a longitudinal axis 29 of the gas bleeder manifold 20.

A first fluid inlet 26 has opposing first and second ends 26a, 26b and defines a second opening on the outer surface 21 at the first end 26a of the first fluid inlet 26. The first fluid inlet 26 extends between the first and second ends 26a, 26b of the first fluid inlet 26 along a first direction 32 forming a first acute angle α with the longitudinal axis 29 of the gas bleeder manifold 20 and a first obtuse angle β with the gas outlet 22.

A second fluid inlet 34 has opposing first and second ends 34a, 34b and defines a third opening on the outer surface 21 at the first end 34a of the second fluid inlet 34. The second fluid inlet 34 extends between the first and second ends 34a, 34b of the second fluid inlet 34 along a second direction 36 forming a second acute angle γ with the longitudinal axis 29 of the gas bleeder manifold 20 and a second obtuse angle δ with the gas outlet 22.

An internal fluid passage 28 fluidly couples the gas outlet 22 to the first and second fluid inlets 26, 34 such that a fluid can flow from the first fluid inlet 26 to the second fluid inlet 34 and gases transported by the fluid can exit the gas bleeder manifold 20 through the gas outlet 22. The internal fluid passage 28 is substantially Y-shaped as viewed in cross-section in certain embodiments. Further, the internal fluid passage 28 may include a first portion 28a extending from the second end 26b of the first fluid inlet 26, a second portion 28b extending from the second end 34b of the second fluid inlet 34, and a third portion 28c extending from the second end 22b of the gas outlet portion 22.

In certain embodiments of the present disclosure, the first portion of the internal fluid passage 28a extends along the first direction 32 forming an acute angle α with the longitudinal axis 29, the second portion of the internal fluid passage 28b extends along the second direction 36 forming an acute angle γ with the longitudinal axis 29, and the third portion of the internal fluid passage 28c extends along the longitudinal axis 29. In certain embodiments, the first, second, and third portions of the internal fluid passage 28a, 28b, 28c adjoin each other or are otherwise fluidly communicable at a common junction 28d.

In certain embodiments of the disclosure, the dynamic fluid gas bleeder manifold 20 includes weep holes for relieving excess pressure in the manifold 20. In certain embodiments, a first weep hole 24a extends from the gas outlet 22 to the outer surface 21 of the gas bleeder manifold 20, a second weep hole 24b extends from the first fluid inlet 26 to the outer surface 21 of the gas bleeder manifold 20, and a third weep hole 24c extends from the second fluid inlet 34 to the outer surface 21 of the gas bleeder 20. Each fluid inlet 26, 34 and the gas outlet 22 includes weep holes 24a, 24b, 24c, in certain embodiments. Weep holes detect leaks in seals, primarily from under-tightened fittings.

Figure 8:
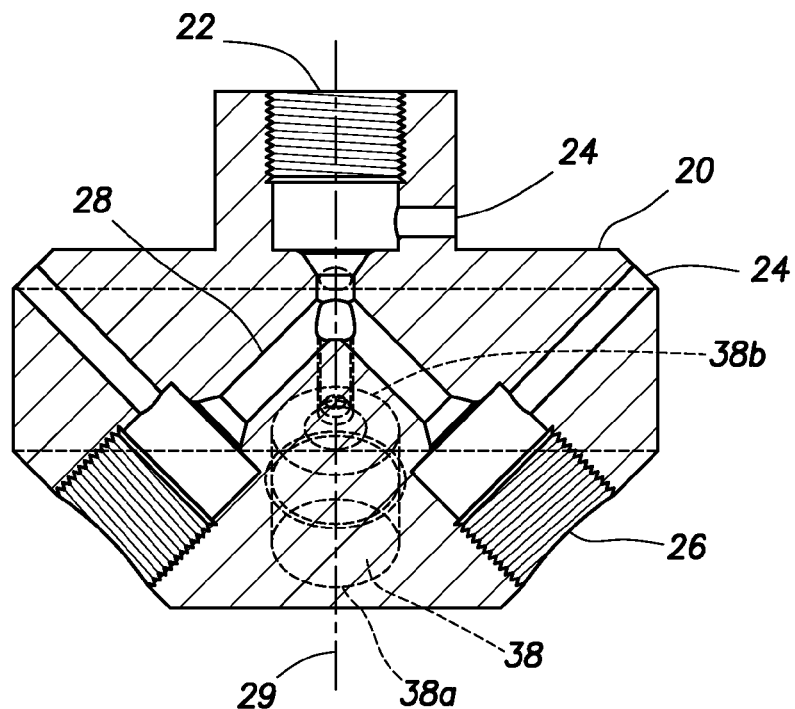
FIG. 8 is a cross-sectional view of a dynamic fluid gas bleeder manifold according to an embodiment of the present disclosure.

In certain embodiments of the disclosure, the dynamic fluid gas bleeder manifold 20 further includes additional fluid inlets, as shown in phantom in FIG. 8. For example, a third fluid inlet 38 has opposing first and second ends 38a, 38b and defines a fourth opening on the outer surface 21 at the first end 38a of the third fluid inlet 38. The third fluid inlet 38 extends between the first and second ends of the third fluid inlet 38a, 38b along a third direction forming a third acute angle (not indicated) with the longitudinal axis 29 and a third obtuse angle (not indicated) with the gas outlet 22. The internal fluid passage 28 connects the gas outlet 22 to the third fluid inlet 38.

In certain embodiments, the dynamic fluid gas bleeder manifold 20 may include a fourth or more additional fluid inlets. While not depicted in FIG. 8 (but see FIG. 9C), a fourth fluid inlet could be located on an opposite side of the manifold 20 from the third inlet 38. Therefore, the fourth inlet would project out of the page in the view illustrated in FIG. 8. Like the first, second, and third fluid inlets, the fourth fluid inlet may have opposing first and second ends and may define a fifth opening formed on the outer surface of the gas bleeder manifold 21 at the first end of the fourth fluid inlet. The fourth fluid inlet may extend between the first and second ends of the fourth fluid inlet along a fourth direction forming a fourth acute angle with the longitudinal axis 29 of the gas bleeder manifold 20 and a fourth obtuse angle with the gas outlet 22. The internal fluid passage 28 may also connect the gas outlet 22 to the fourth fluid inlet.

Figure 9A:
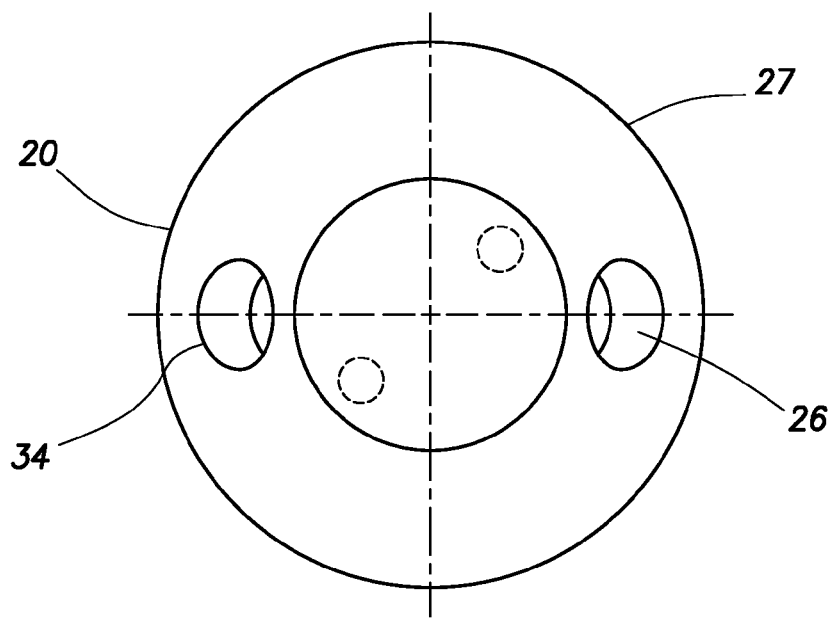
FIGS. 9A-9C are bottom views of dynamic fluid gas bleeder manifolds according to embodiments of the present disclosure.
Figure 9B:
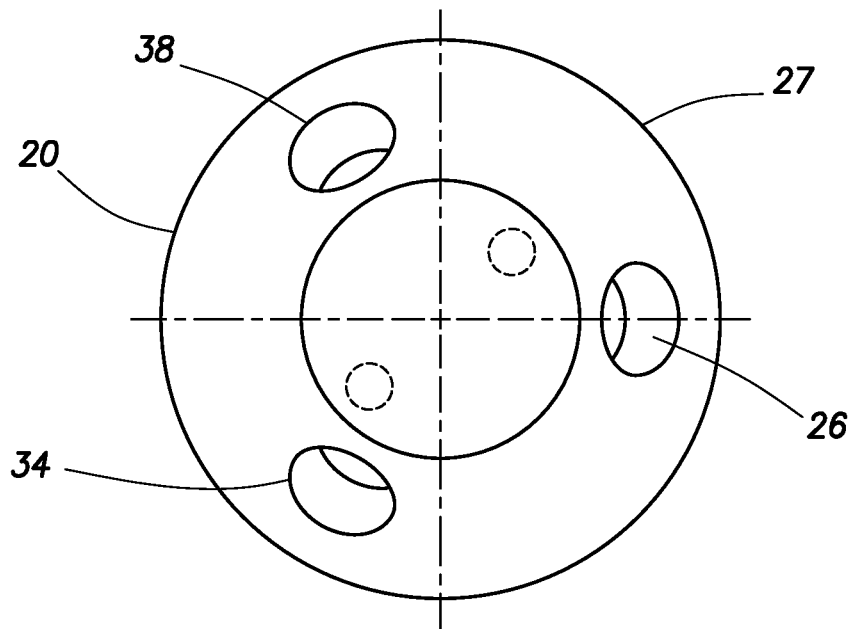
Figure 9C:
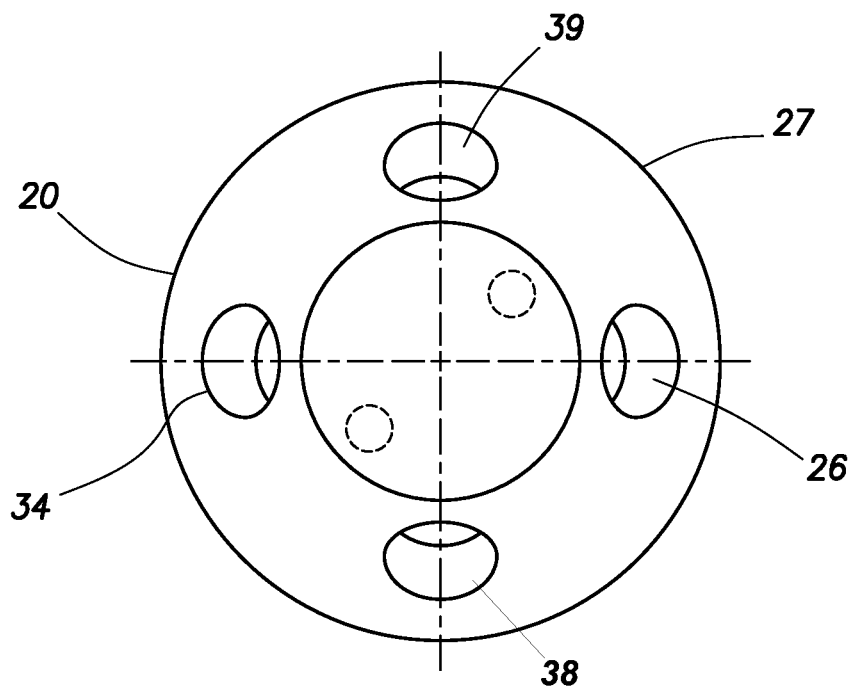

Adverting to FIGS. 9A-9C, locations of the plurality of fluid inlets are shown for certain embodiments of the present disclosure in bottom views of the lower portion 27 of the manifold 20. As shown in FIG. 9A, a manifold 20 with two fluid inlets may be arranged with the first fluid inlet 26 and second fluid inlet 34 on opposing sides of the manifold 20, in certain embodiments. In a manifold 20 with three fluid inlets, the first, second, and third fluid inlets 26, 34, 38 may be arranged at approximately 120° angular orientation, as shown in FIG. 9B. Similarly, when a manifold 20 has four fluid inlets, the first, second, third, and fourth fluid inlets 26, 34, 38, 39 may be arranged at approximately 90° intervals, as shown in FIG. 9C. Those skilled in the art will readily recognize that the illustrated orientation of the fluid inlets does not limit relative locations of a plurality of fluid inlets according to the present disclosure.

Figure 10:
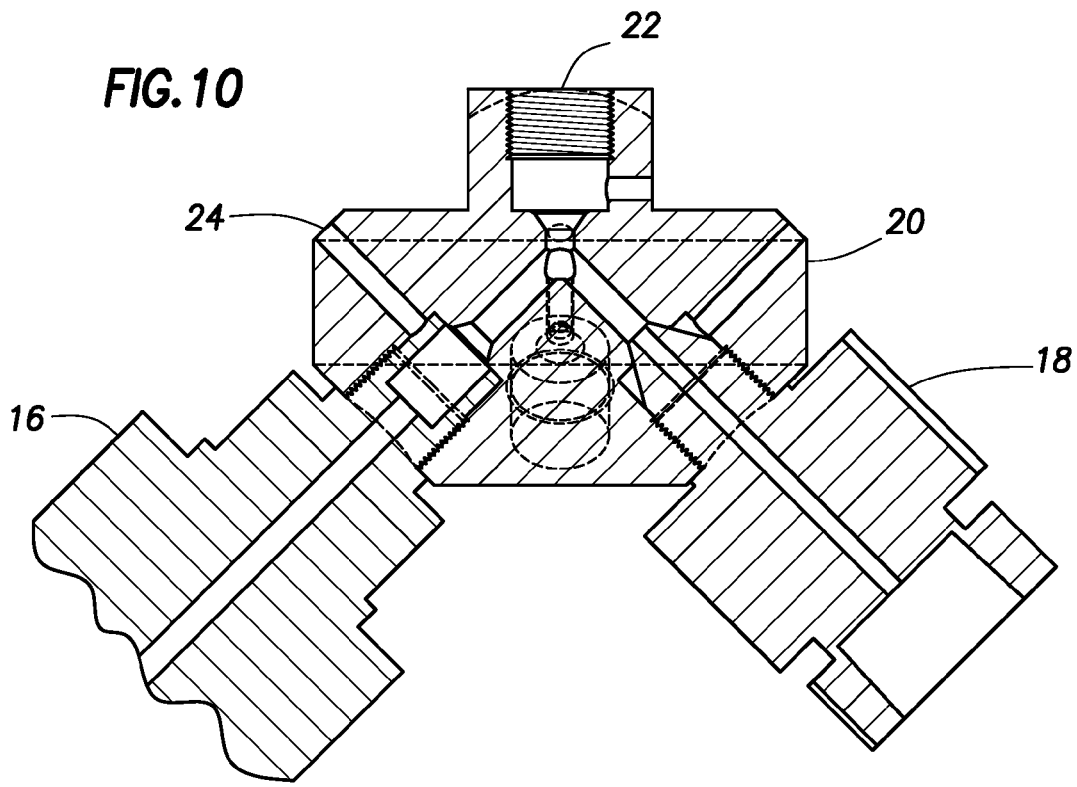
FIG. 10 is a cross-sectional view of a dynamic fluid gas bleeder manifold with a sensor attached according to an embodiment of the present disclosure.

The geometry of the gas bleeder manifold 20, according to certain embodiments of the present disclosure, allows gas in the internal fluid passage 28 to flow toward the gas outlet 22, where the gas may be collected and released. In certain embodiments of the present disclosure, a valve may be connected to the gas outlet 22 to allow the purging of gas collected in the gas outlet 22. The geometry of the manifolds 20 of the present disclosure may prove advantageous in preventing gas pockets from forming at locations where sensors 16 may be attached to the manifold 20, as shown in FIG. 10, thus allowing accurate measurements of fluid parameters such as temperature and pressure, to be made.

Dynamic fluid gas bleeder manifolds according to the present disclosure can be made of any material suitable for withstanding the pressure to which the manifold will be subjected. For high pressure applications, a metal, such as steel, is desirable. Manifolds, according to certain embodiments of the present disclosure, may be able to withstand pressures of up to 150,000 psi or more. The manifold can accommodate any diameter high pressure tubing at the fluid inlets. For example, a manifold can include high pressure tubing of a variety of diameters at the fluid inlets. In certain embodiments, the manifold can accommodate ¼ to 1 inch diameter high pressure tubing at the fluid inlets. The tubing can be attached to the manifold by any appropriate means such as by screwing threaded tubing into the inlet, welding, o-ring fitting, and any equivalent means.

Figure 11:
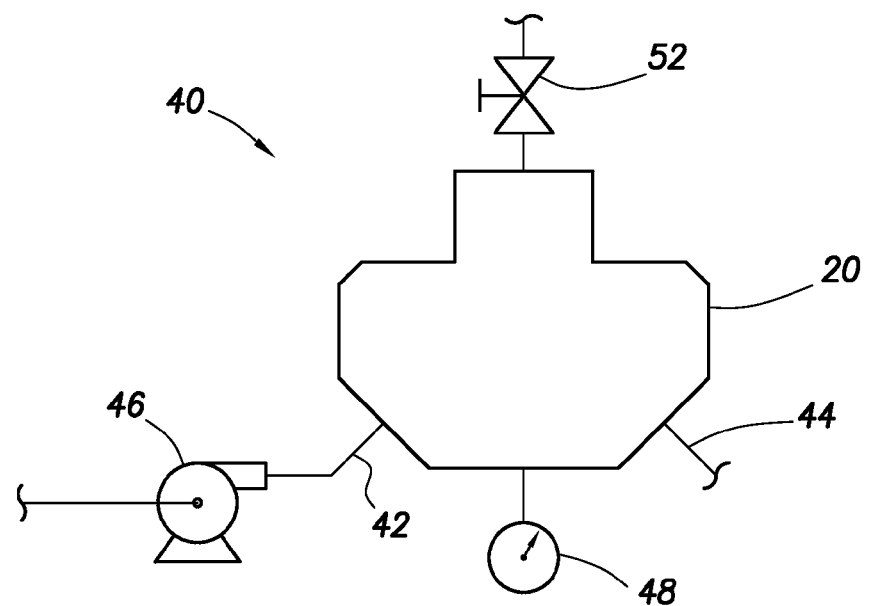
FIG. 11 is a schematic view of high pressure fluid test system according to an embodiment of the present disclosure.

In certain embodiments of the disclosure, a high pressure dynamic fluid test system 40 is provided, as illustrated in FIG. 11. The high pressure dynamic test 40, according to one or more embodiments of the present disclosure, may include a dynamic fluid gas bleeder manifold 20, a pump 46 fluidly coupled to the gas bleeder manifold 20 and configured to convey a fluid thereto, and a sensor 48 fluidly coupled to the gas bleeder manifold 20 and configured to measure a parameter of the fluid.

In certain embodiments of the present disclosure, the sensor 48 measures a pressure or a temperature of the fluid. The sensor 48 may be fluidly coupled to the gas bleeder manifold 20 through one of the fluid inlets. Fluid flows through the manifold via inlet tubing 42 and outlet tubing 44 attached to the manifold 20 at the fluid inlets.

In certain embodiments of the present disclosure, a valve 52 may be fluidly coupled to the gas bleeder manifold 20 through the gas outlet 22. When the high pressure dynamic fluid test system 40 is in operation the gas bleeder manifold 20 is oriented so that the longitudinal axis 29 is oriented in a vertical direction, and the gas outlet 22 is located above the first and second fluid inlets 26, 34 in the vertical direction.

In certain embodiments of the present disclosure a method for high pressure testing a fluid is provided. The method may include providing a high pressure test system 40 comprising a dynamic fluid gas bleeder manifold 20. The manifold 20 may include a gas outlet 22 having opposing first and second ends 22a, 22b and defining a first opening on an outer surface 21 at the first end of the gas outlet 22a. The gas outlet 22 extends between the first and second ends 22a, 22b of the gas outlet 22 along a longitudinal axis 29 of the gas bleeder manifold 20. A first fluid inlet 26 has opposing first and second ends 26a, 26b and defines a second opening on the outer surface 21 at the first end 26a of the first fluid inlet 26. The first fluid inlet 26 extends between the first and second ends of the first fluid inlet 26a, 26b along a first direction 32 forming a first acute angle α with the longitudinal axis 29 of the gas bleeder manifold 20 and a first obtuse angle β with the gas outlet 22. A second fluid inlet 34 has opposing first and second ends 34a, 34b and defines a third opening on the outer surface 21 at the first end 34a of the second fluid inlet 34. The second fluid inlet 34 extends between the first and second ends of the second fluid inlet 34a, 34b along a second direction 36 forming a second acute angle γ with the longitudinal axis 29 of the gas bleeder manifold 20 and a second obtuse angle δ with the gas outlet 22. An internal fluid passage 28 fluidly couples the gas outlet 22 to the first and second fluid inlets 26, 34 such that a fluid can flow from the first fluid inlet 26 to the second fluid inlet 34 and gases transported by the fluid can exit the gas bleeder manifold 20 through the gas outlet 22. A pump 46 communicates with the gas bleeder manifold 20 to pump the fluid, and a sensor 16 measures a parameter of the fluid. The method may further include providing a fluid to the high pressure test system 40. The fluid is pumped to increase the pressure on the fluid, and a parameter of the fluid is measured, such as pressure or temperature.

In certain embodiments of the present disclosure, the fluid is a cement. The high pressure test system 40 simulates a downhole condition, in certain embodiments. In certain embodiments, the parameter measured is a pressure or a temperature of the fluid.

In certain embodiments of the present disclosure, the method for high pressure testing a fluid further includes separating gases from the fluid, conveying the separated gases to the gas outlet, and discharging the separated gases from the gas bleeder manifold 20 via the gas outlet 22.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A dynamic fluid gas bleeder manifold comprising:
a gas outlet having opposing first and second ends and defining a first opening on an outer surface of the manifold at the first end of the gas outlet, wherein said gas outlet extends between the first and second ends of the gas outlet along a longitudinal axis of the gas bleeder manifold;
a first fluid inlet having opposing first and second ends and defining a second opening on the outer surface at the first end of the first fluid inlet, wherein said first fluid inlet extends between the first and second ends of the first fluid inlet along a first direction forming a first acute angle with the longitudinal axis, and forming a first obtuse angle with the gas outlet;
a second fluid inlet having opposing first and second ends and defining a third opening on the outer surface at the first end of the second fluid inlet, wherein said second fluid inlet extends between the first and second ends of the second fluid inlet along a second direction forming a second acute angle with the longitudinal axis, and forming a second obtuse angle with the gas outlet;
an unobstructed weep hole extending from at least one of the gas outlet, the first fluid inlet, and the second fluid inlet to and in constant fluid communication with the outer surface of the manifold, and thereby providing direct fluid communication to a surrounding atmosphere; and
an internal fluid passage fluidly coupling the gas outlet to the first and second fluid inlets such that a fluid can flow from said first fluid inlet to said second fluid inlet and gases transported by said fluid can exit the gas bleeder manifold through said gas outlet.

2. The dynamic fluid gas bleeder manifold according to claim 1, wherein said gas bleeder manifold is substantially circular-shaped as viewed in plan view.

3. The dynamic fluid gas bleeder manifold according to claim 1, wherein said internal fluid passage is substantially Y-shaped as viewed in cross-sectional view.

4. The dynamic fluid gas bleeder manifold according to claim 1, wherein said internal fluid passage comprises a first portion of the internal fluid passage extending from the second end of the first fluid inlet, a second portion of the internal fluid passage extending from the second end of the second fluid inlet, and a third portion of the internal fluid passage extending from the second end of the gas outlet portion.

5. The dynamic fluid gas bleeder manifold according to claim 4, wherein said first portion of the internal fluid passage extends along the first direction, the second portion of the internal fluid passage extends along the second direction, and the third portion of the internal fluid passage extends along the longitudinal axis.

6. The dynamic fluid gas bleeder manifold according to claim 5, wherein the first, second, and third portions of the internal fluid passage adjoin each other at a common junction.

7. The dynamic fluid gas bleeder manifold according to claim 1, further comprising a third fluid inlet having opposing first and second ends and defining a fourth opening on the outer surface at the first end of the third fluid inlet, wherein said third fluid inlet extends between the first and second ends of the third fluid inlet along a third direction forming a third acute angle with the longitudinal axis, and forming a third obtuse angle with the gas outlet, wherein
the internal fluid passage connects said gas outlet to said third fluid inlet.

8. The dynamic fluid gas bleeder manifold according to claim 7, further comprising a fourth fluid inlet having opposing first and second ends and defining a fifth opening on the outer surface at the first end of the fourth fluid inlet, wherein said fourth fluid inlet extends between the first and second ends of the fourth fluid inlet along a fourth direction forming a fourth acute angle with the longitudinal axis of the gas bleeder manifold, and forming a fourth obtuse angle with the gas outlet, wherein
the internal fluid passage connects said gas outlet to said fourth fluid inlet.

9. The dynamic fluid gas bleeder manifold according to claim 1, wherein the unobstructed weep hole is defined in the manifold between the first and second ends of the at least one of the gas outlet, the first fluid inlet, and the second fluid inlet.

10. A high pressure dynamic fluid test system comprising:
a dynamic fluid gas bleeder manifold comprising:
a gas outlet having opposing first and second ends and defining a first opening on an outer surface at the first end of the gas outlet, wherein said gas outlet extends between the first and second ends of the gas outlet along a longitudinal axis of the gas bleeder manifold;
a first fluid inlet having opposing first and second ends and defining a second opening on the outer surface at the first end of the first fluid inlet, wherein said first fluid inlet extends between the first and second ends of the first fluid inlet along a first direction forming a first acute angle with the longitudinal axis, and forming a first obtuse angle with the gas outlet;
a second fluid inlet having opposing first and second ends and defining a third opening on the outer surface at the first end of the second fluid inlet, wherein said second fluid inlet extends between the first and second ends of the second fluid inlet along a second direction forming a second acute angle with the longitudinal axis, and forming a second obtuse angle with the gas outlet;
an unobstructed weep hole extending from at least one of the gas outlet, the first fluid inlet, and the second fluid inlet to and in constant fluid communication with the outer surface of the manifold, and thereby providing direct fluid communication to a surrounding atmosphere; and
an internal fluid passage fluidly coupling the gas outlet to the first and second fluid inlets such that a fluid can flow from said first fluid inlet to said second fluid inlet and gases transported by said fluid can exit the gas bleeder manifold through said gas outlet;
a pump fluidly coupled to said gas bleeder manifold and configured to convey the fluid thereto; and
a sensor fluidly coupled to the gas bleeder manifold and configured to measure a parameter of the fluid.

11. The high pressure dynamic fluid test system of claim 10, wherein the parameter is a pressure or a temperature of the fluid.

12. The high pressure dynamic fluid test system of claim 10, wherein the sensor is fluidly coupled to the gas bleeder manifold through a third fluid inlet.

13. The high pressure dynamic fluid test system of claim 10, further comprising a valve fluidly coupled to the gas bleeder manifold through the gas outlet.

14. The high pressure dynamic fluid test system of claim 10, wherein, when the high pressure dynamic fluid test system is in operation, the gas bleeder manifold is oriented so that the longitudinal axis is oriented in a vertical direction, and the gas outlet is located above the first and second fluid inlets in the vertical direction.

15. The high pressure dynamic fluid test system of claim 10, wherein the unobstructed weep hole is defined in the manifold between the first and second ends of the at least one of the gas outlet, the first fluid inlet, and the second fluid inlet.

16. A method for high pressure testing a fluid, comprising:
providing a high pressure test system that includes a dynamic fluid gas bleeder manifold, the dynamic fluid gas bleeder manifold comprising:
  a gas outlet having opposing first and second ends and defining a first opening on an outer surface at the first end of the gas outlet, and said gas outlet extends between the first and second ends of the gas outlet along a longitudinal axis of the gas bleeder manifold;
  a first fluid inlet having opposing first and second ends and defining a second opening on the outer surface at the first end of the first fluid inlet, wherein said first fluid inlet extends between the first and second ends of the first fluid inlet along a first direction forming a first acute angle with the longitudinal axis, and forming a first obtuse angle with the gas outlet;
  a second fluid inlet having opposing first and second ends and defining a third opening on the outer surface at the first end of the second fluid inlet, wherein said second fluid inlet extends between the first and second ends of the second fluid inlet along a second direction forming a second acute angle with the longitudinal axis, and forming a second obtuse angle with the gas outlet;
  an unobstructed weep hole extending from at least one of the gas outlet, the first fluid inlet, and the second fluid inlet to and in constant fluid communication with the outer surface of the manifold, and thereby providing direct fluid communication to a surrounding atmosphere; and
  an internal fluid passage fluidly coupling the gas outlet to the first and second fluid inlets such that a fluid can flow from said first fluid inlet to said second fluid inlet and gases transported by said fluid can exit the gas bleeder manifold through said gas outlet;
  a pump communicating with said gas bleeder manifold to pump the fluid; and
  a sensor for measuring a parameter of the fluid;
providing a fluid to the high pressure test system;
pumping the fluid to increase a pressure on the fluid; and
measuring a parameter of the fluid.

17. The method for high pressure testing a fluid according to claim 16, wherein the fluid is a cement.

18. The method for high pressure testing a fluid according to claim 17, wherein measuring the parameter further comprises measuring a pressure or a temperature of the fluid.

19. The method for high pressure testing a fluid according to claim 16, wherein the high pressure testing simulates a downhole condition.

20. The method for high pressure testing a fluid according to claim 16, further comprising:
separating gases from the fluid;
conveying the gases to the gas outlet; and
discharging the gases from the gas bleeder manifold via the gas outlet.

\* \* \* \* \*